(12) United States Patent
Sysko et al.

(10) Patent No.: US 10,937,535 B1
(45) Date of Patent: *Mar. 2, 2021

(54) METHODS AND SYSTEMS FOR MANAGING PATIENT TREATMENT COMPLIANCE

(71) Applicant: Welldoc, Inc., Columbia, MD (US)

(72) Inventors: Ryan Sysko, Wilmington, DE (US); Chris Bergstrom, Millersville, MD (US)

(73) Assignee: Welldoc, Inc., Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/074,442

(22) Filed: Oct. 19, 2020

Related U.S. Application Data

(63) Continuation of application No. 15/839,446, filed on Dec. 12, 2017, now Pat. No. 10,839,951, which is a (Continued)

(51) Int. Cl.
*G16H 20/13* (2018.01)
*G16H 50/20* (2018.01)
*G06Q 10/10* (2012.01)
*G06Q 40/08* (2012.01)
*G16H 20/10* (2018.01)
*G16H 10/60* (2018.01)
(Continued)

(52) U.S. Cl.
CPC ............ *G16H 20/13* (2018.01); *G06Q 10/10* (2013.01); *G06Q 40/08* (2013.01); *G16H 10/60* (2018.01); *G16H 15/00* (2018.01); *G16H 20/00* (2018.01); *G16H 20/10* (2018.01); *G16H 40/20* (2018.01); *G16H 50/20* (2018.01); *G16H 40/67* (2018.01); *G16H 80/00* (2018.01)

(58) Field of Classification Search
None
See application file for complete search history.

(56) References Cited

U.S. PATENT DOCUMENTS 5,933,136 A 8/1999 Brown
2003/0208113 A1 11/2003 Mault et al.
(Continued)

OTHER PUBLICATIONS

Mohana Ravindranath, "Well Doc to release prescription-only smartphone app", Jun. 23, 2013, The Washington Post (2 pages).
(Continued)

*Primary Examiner* — Devin C Hein
(74) *Attorney, Agent, or Firm* — Bookoff McAndrews, PLLC

(57) ABSTRACT

Provided are computer implemented method and systems for providing and monitoring patient compliance with a patient healthcare treatment plan. The method includes receiving, from a healthcare provider over a network, application features for generating a patient application including patient instructions for using a medical therapy, and generating an application for a patient. The application includes at least an input for the user to input data for use in evaluating patient compliance with a treatment plan. In addition, the method includes receiving, from the healthcare provider over the network, a prescription for the application for the patient, and activating the application after the patient receives training on use of the application. The method also may include receiving patient compliance data from the application over the network based on the input.

20 Claims, 14 Drawing Sheets

Related U.S. Application Data continuation of application No. 14/516,015, filed on Oct. 16, 2014, now Pat. No. 9,881,136.

(60) Provisional application No. 61/892,151, filed on Oct. 17, 2013.

(51) Int. Cl.
*G16H 15/00* (2018.01)
*G16H 20/00* (2018.01)
*G16H 80/00* (2018.01)
*G16H 40/67* (2018.01)
*G16H 40/20* (2018.01)

(56) References Cited

U.S. PATENT DOCUMENTS

| | | |
|---|---|---|
| 2005/0144038 A1 | 6/2005 | Tamblyn et al. |
| 2007/0055552 A1 | 3/2007 | St. Clair et al. |
| 2010/0069730 A1 | 3/2010 | Bergstrom et al. |
| 2011/0125521 A1 | 5/2011 | Dhoble |
| 2012/0253833 A1 | 10/2012 | John et al. |
| 2013/0226618 A1 | 8/2013 | Eisenhandler et al. |
| 2014/0089011 A1 | 3/2014 | Fletcher |
| 2014/0325065 A1 | 10/2014 | Birtwhistle et al. |

OTHER PUBLICATIONS

Anita Campbell, "What the Heck is an 'App'?", Mar. 7, 2011, Small Business Trends—https://smallbiztrends.com, <https://smallbiztrends.com/2011/03/what-is-an-app.html/print/>, (4 pages).

METHODS AND SYSTEMS FOR MANAGING PATIENT TREATMENT COMPLIANCE

CROSS-REFERENCE TO RELATED APPLICATIONS

This application is a continuation of U.S. application Ser. No. 15/839,446, filed Dec. 12, 2017, which is a continuation of U.S. application Ser. No. 14/516,015, filed Oct. 16, 2014, now U.S. Pat. No. 9,881,136, which claims priority to U.S. Provisional Application No. 61/892,151, entitled "Methods and Systems for Managing Patient Treatment Compliance", filed Oct. 17, 2013, the entireties of each of which are incorporated by reference herein.

TECHNICAL FIELD

The present disclosure generally relates to patient monitoring. More specifically, the present disclosure relates to methods and systems for monitoring patient behavior and treatment compliance as well as reducing fraud and waste of pharmaceutical and medical products including, e.g., prescribed therapies.

BACKGROUND

Physicians often ascertain patient compliance with treatment instructions after subsequent patient visits and evaluation. In some cases, failure to comply with physician treatment instructions may lead to prolonged patient illness and/or worsened patient health. In addition, lack of proper compliance may lead to a waste of medical devices, drugs, or other prescribed therapies. This waste, in turn, may lead to increased medical costs, as well as improper feedback of the physician's treatment plan and/or the efficacy of the prescribed therapy. Further, patient compliance with physician treatment instructions may still fail to provide patients with dynamic information and assistance with managing their disease.

Accordingly, a need exists for methods and systems for monitoring patient behavior and treatment, drug and/or therapy usage, compliance, and improved patient compliance.

SUMMARY

Examples of the present disclosure relate to, among other things, patient monitoring. Each of the examples disclosed herein may include one or more of the features described in connection with any of the other disclosed examples.

In one example, a computer implemented method for providing and monitoring patient compliance with a patient healthcare treatment plan may include receiving, from a healthcare provider over a network, application features for generating a patient application including patient instructions for using a medical therapy. The method also may include generating an application for a patient, the application including at least an input for the patient to input data for use in evaluating patient compliance with the patient healthcare treatment plan. The method also may include receiving, from the healthcare provider over the network, a prescription for the application for the patient, activating the application after the patient receives at least one instruction on use of the application, and receiving patient compliance data from the application over the network based on the input.

Examples of the method may include one or more of the following features: further comprising a step of providing, via the network, a notification to a dispenser to refill a patient prescription for the medical therapy based on the patient compliance data; the step of activating the application may comprise receiving, over the network, instructions from a patient's insurance company; the method may further include sending, via the network, a report to the healthcare provider, based on the patient compliance data; wherein the step of generating the application for the patient comprises electronically acquiring a national drug code number from a regulatory entity; wherein the step of receiving patient compliance data may include automatically updating the application based on electronic feedback; wherein the at least one instruction may be conducted online; wherein the step of receiving the application features for generating a patient application may include providing access to an electronic medical record of the patient; further comprising generating a medical profile of the patient based on parsing the electronic medical record of the patient; and further comprising generating electronic feedback to the patient based on electronic processing of the compliance data.

In another example, a system for providing and monitoring compliance with a patient healthcare treatment plan may include a data storage device storing instructions for causing computer servers or mobile devices to one of generate or provide the patient healthcare treatment plan and evaluate patient compliance with the patient healthcare treatment plan. The system also may include a processing device configured to execute instructions to perform a method of: receiving, from a healthcare provider over a network, application features for generating a patient application including patient instructions for using a medical therapy; generating an application for a patient, the application including at least an input for patient to input data for use in evaluating patient compliance with the patient healthcare treatment plan; receiving, from the healthcare provider over the network, a prescription for the application for the patient; activating the application after the patient receives at least one instruction on use of the application; and receiving patient compliance data from the application over the network based on the input.

In another example, a non-transitory computer-readable medium may be configured for storing instructions that, when executed by a processor, cause the processor to provide and monitor compliance with a patient healthcare treatment plan, the instructions may comprise: receiving, from a healthcare provider over a network, application features for generating a patient application including patient instructions for using medication; generating an application for a patient, the application including at least an input for the user to input data for use in evaluating patient compliance with a treatment plan; receiving, from the healthcare provider over the network, a prescription for the application for the patient; and activating the application after the patient receives training on use of the application; and receiving patient compliance data from the application over the network.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments According to some embodiments, disclosed herein is a process that allows healthcare providers to prescribe computer applications or other software programs/algorithms for behavioral monitoring and treatment of their patients.

In one embodiment, the process includes a means where an exemplary application, such as a mobile health (mHealth) application, is used by a patient as part of his/her healthcare treatment plan in order to introduce proactive thinking into health consciousness of the patient.

In another embodiment, the process may include a means that may allow the healthcare provider to have an outside system monitor the health of their patient and relieve the burden associated with proactive health care from healthcare providers.

Still further, the process may include a means where the prescription event (post hoc treatment of symptoms) becomes event-related to proactive treatment and management of patient disease.

In another aspect, it is further contemplated to introduce a mobile health (mHealth) application usage as a service to all entities in a health care system, including pharmaceutical companies, the healthcare providers, patients, retailers, pharmacies, and health insurance companies.

In another embodiment, it is contemplated to reduce fraud and abuse by introducing patient compliance with a mobile health (mHealth) application as a parameter for successful treatment of a disease.

DETAILED DESCRIPTION

Reference will now be made in detail to the exemplary embodiments of the disclosure, examples of which are illustrated in the accompanying drawings. Wherever possible, the same reference numbers will be used throughout the drawings to refer to the same or like parts.

The present disclosure describes systems and methods for monitoring of patient behavior and treatment compliance as well as reducing fraud and waste of pharmaceutical and medical products and/or therapies.

Figure 1:
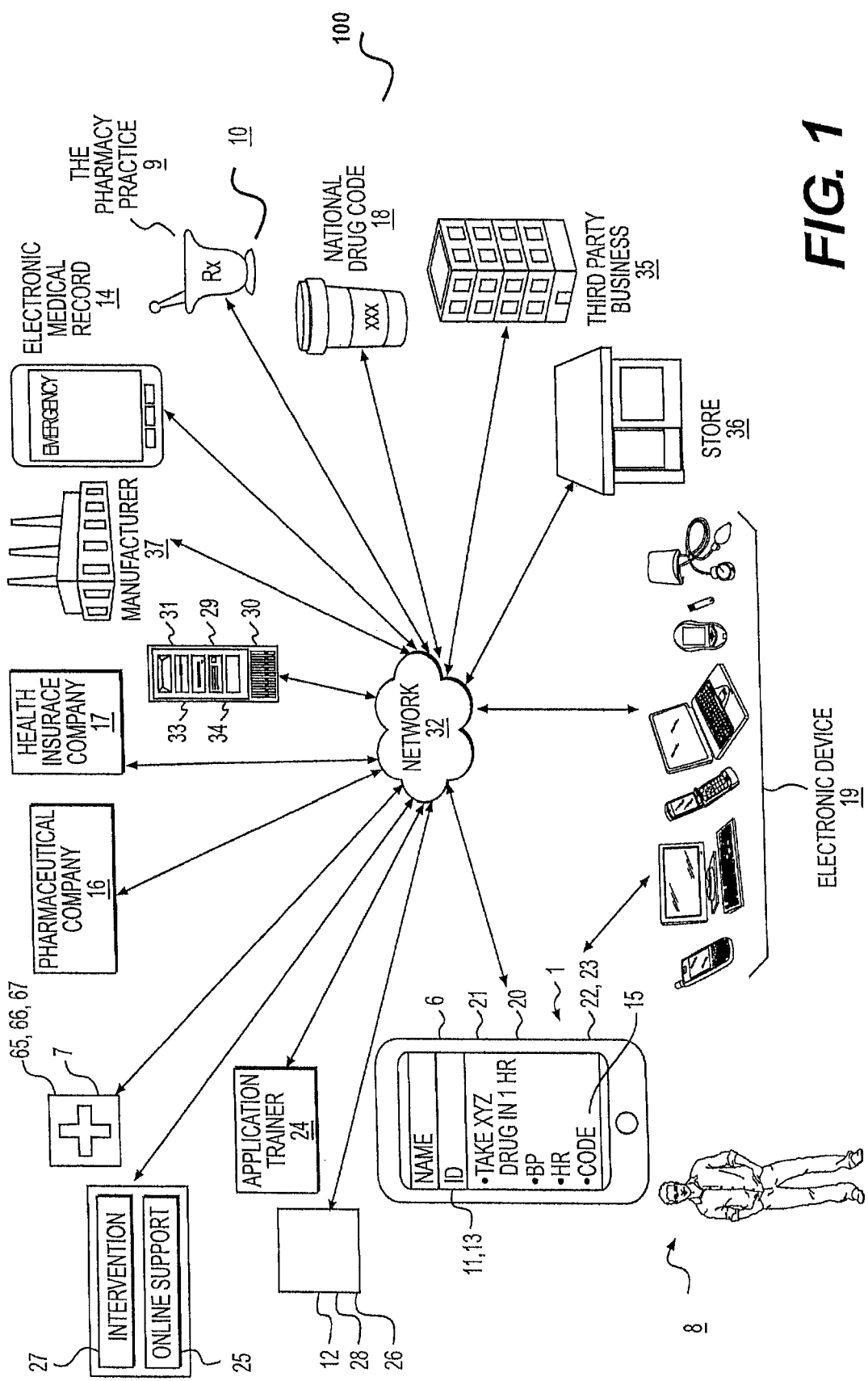
FIG. 1 is a block diagram of a patient monitoring system configured to provide online monitoring of patient treatment compliance, according to an exemplary embodiment of the present disclosure.

FIG. 1 is a block diagram of a patient monitoring system 100 configured to provide online monitoring of patient treatment compliance, according to an exemplary embodiment of the present disclosure. A patient 8 having an electronic device 19, such as a mobile device, computer, medical device, or any other electronic device configured to access an electronic network 32, such as the Internet, may communicate with or otherwise access a mobile health (mHealth) application 1. The mHealth application may include patient identifying information, treatment regimen, information about treatments and healthcare, and any other relevant information and may be in communication with other entities or networks to send and receive information. A healthcare provider 7, such as a physician, may prescribe the application. The mHealth application 1 may be tailored to a specific patient and may be activated in person by the patient by visiting a pharmacy 10 or pharmacy practice 9 or other authorized entity. The patient 8 may receive training on using the mHealth application 1 by a mHealth support system 25 and/or application trainer 24. The mHealth application 1 may include programming 28 of various forms, such as machine learning programming algorithms 26.

The patient treatment plan may include a prescription (e.g. for a drug, device, and/or therapy), which may be dispensed by the pharmacy 9. The pharmacy 9 may allow the refill of the prescribed product/therapy after receiving authorization based on the patient's compliance with his/her healthcare treatment plan. The authorization may be received by the pharmacy 10 by a communication from the application 1, via the network 32 and various servers 29. Use of the drug or other medical product/therapy also may be sent to the manufacturer 37 over the network 32 to inform the manufacturer 37 of the amount of medical product or therapy being used by patient 8. This information may assist the manufacturer 37 in assessing demand and planning supply of the medical product or therapy. The healthcare provider 7 also may receive a report based on the patient information received by the application 1, and may update the patient treatment plan based on this information. The patient's electronic medical record 14 also may be automatically electronically updated via the network 32 based on the patient information, which may include electronically transmitted patient feedback on the application, received by the mHealth application 1.

Figure 2:
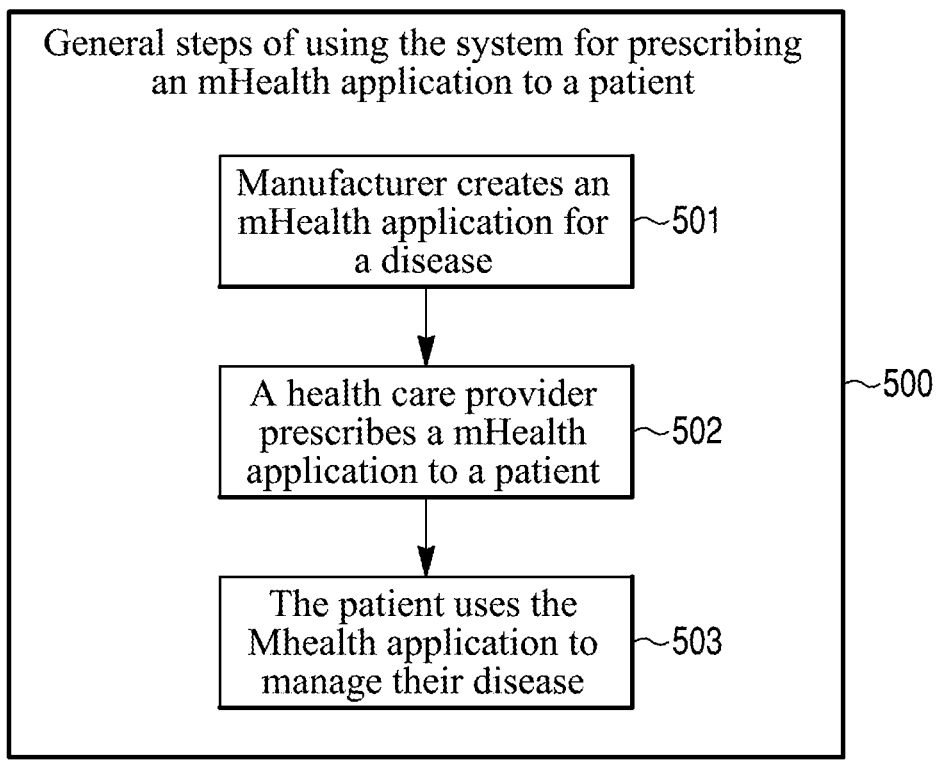
FIG. 2 is a diagrammed series of steps view showing steps of using a system for prescribing a mobile health application to a patient, according to an exemplary embodiment of the present disclosure.

Referring now to FIG. 2, method 500 may include a first step 501 in which the manufacturer 37 creates an mHealth application 1 for a disease. The application 1 may be any set of instructions for execution by an electronic device 19 having a processor and memory. Examples of the electronic device 19 may include a mobile device, a computer, a personal digital assistant, a tablet, a medical device (e.g., an insulin pen, a patch, an implantable or ingestible chip, or any other suitable electronic device). The healthcare provider 7 (e.g., primary care physician, specialist, or any other medical professional with prescribing authority) may prescribe the mHealth application 1 to the patient 8, at step 502. The patient 8 then may use the mHealth application 1 to manage a disease at step 503.

Figure 3:
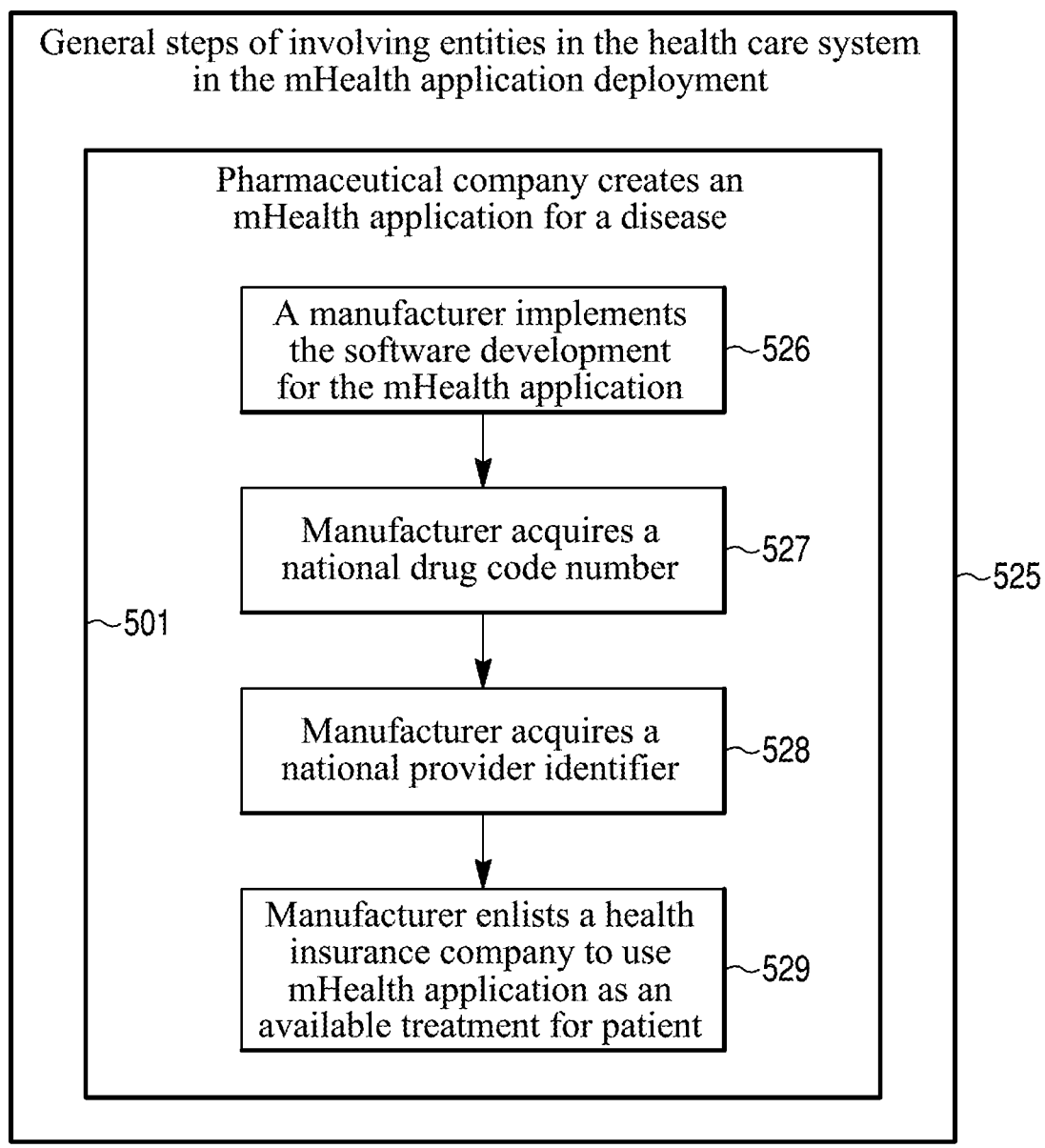
FIG. 3 is a diagrammed method view showing steps of involving entities in a health care system in a mobile health application deployment, according to an exemplary embodiment of the present disclosure.

As shown in FIG. 3, step 501 in FIG. 1 may include several sub steps. For example, at step 526, the manufacturer 37 (e.g. a pharmaceutical company) may implement software development 12 for the mHealth application 1 for a disease 2. The manufacturer 37 also may acquire a national drug code 18 number at step 527, for example from a regulatory entity, such as the Food and Drug Administration. At step 528, the manufacturer 37 may acquire a national provider identifier 13 so that healthcare provider 7 can electronically denote the service as a prescription to the patient 8. The manufacturer 37 may enlist a health insurance company 17 to use the mHealth application 1 as an available treatment for the patient 8 at step 529.

Figure 4:
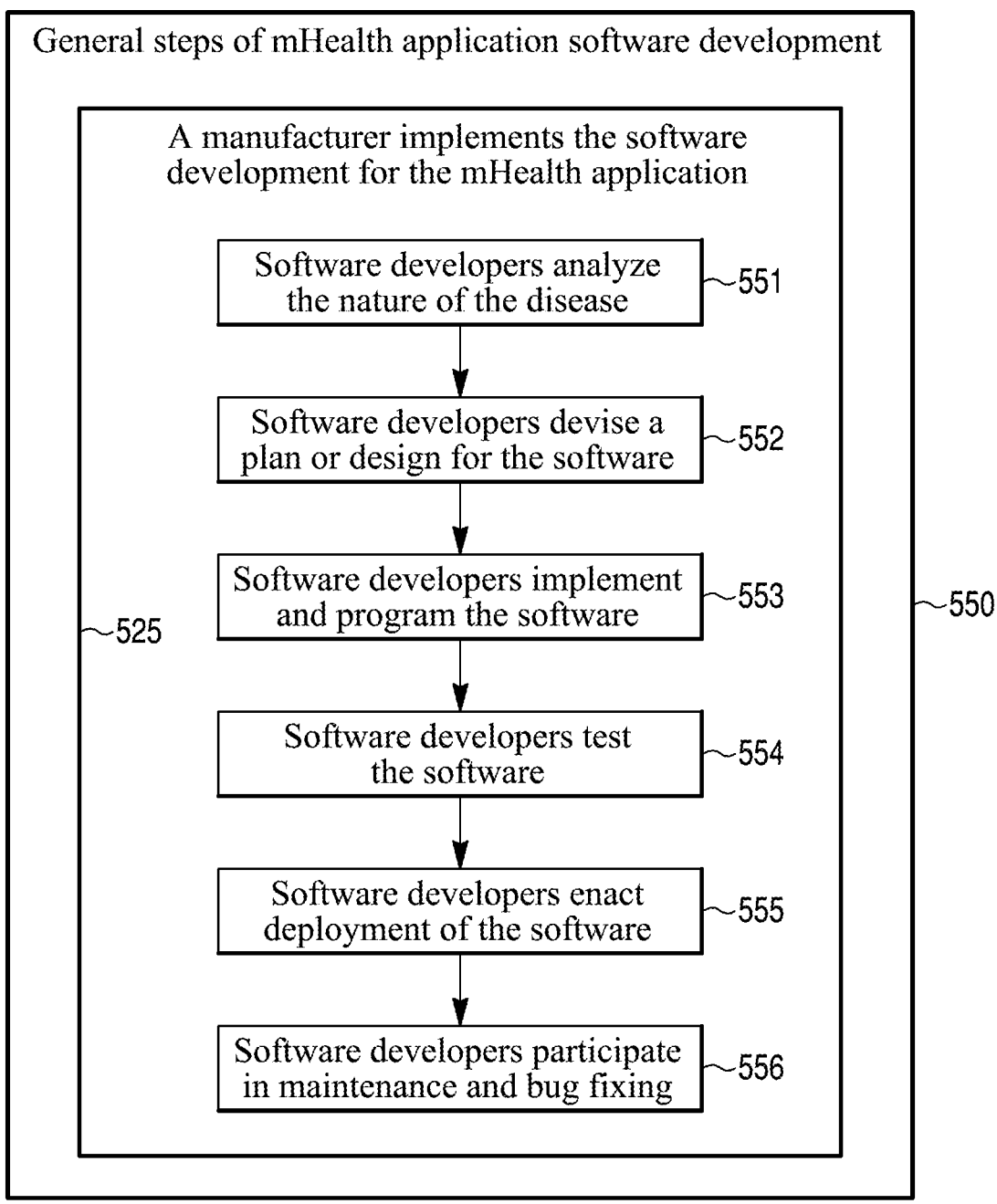
FIG. 4 is a diagrammed method view showing steps of developing mobile heath application software, according to an exemplary embodiment of the present disclosure.

Referring now to FIG. 4, step 526 shown in FIG. 3 may further include several sub steps collectively referred to as method 550. For example, at step 551, the manufacturer 37 may electronically automatically analyze the nature of the disease 2. In addition, the manufacturer 37 may devise and implement a plan or design for the software 6, at step 552. The manufacturer 37 may implement the programming 28 of the software 6, at step 553. At step 554, the manufacturer 37 may test the software 6 and at step 555, the manufacturer 37 may deploy the software 6. The manufacturer 37 also may engage in maintenance, updating, and bug fixing of the software 6, at step 556.

Figure 5:
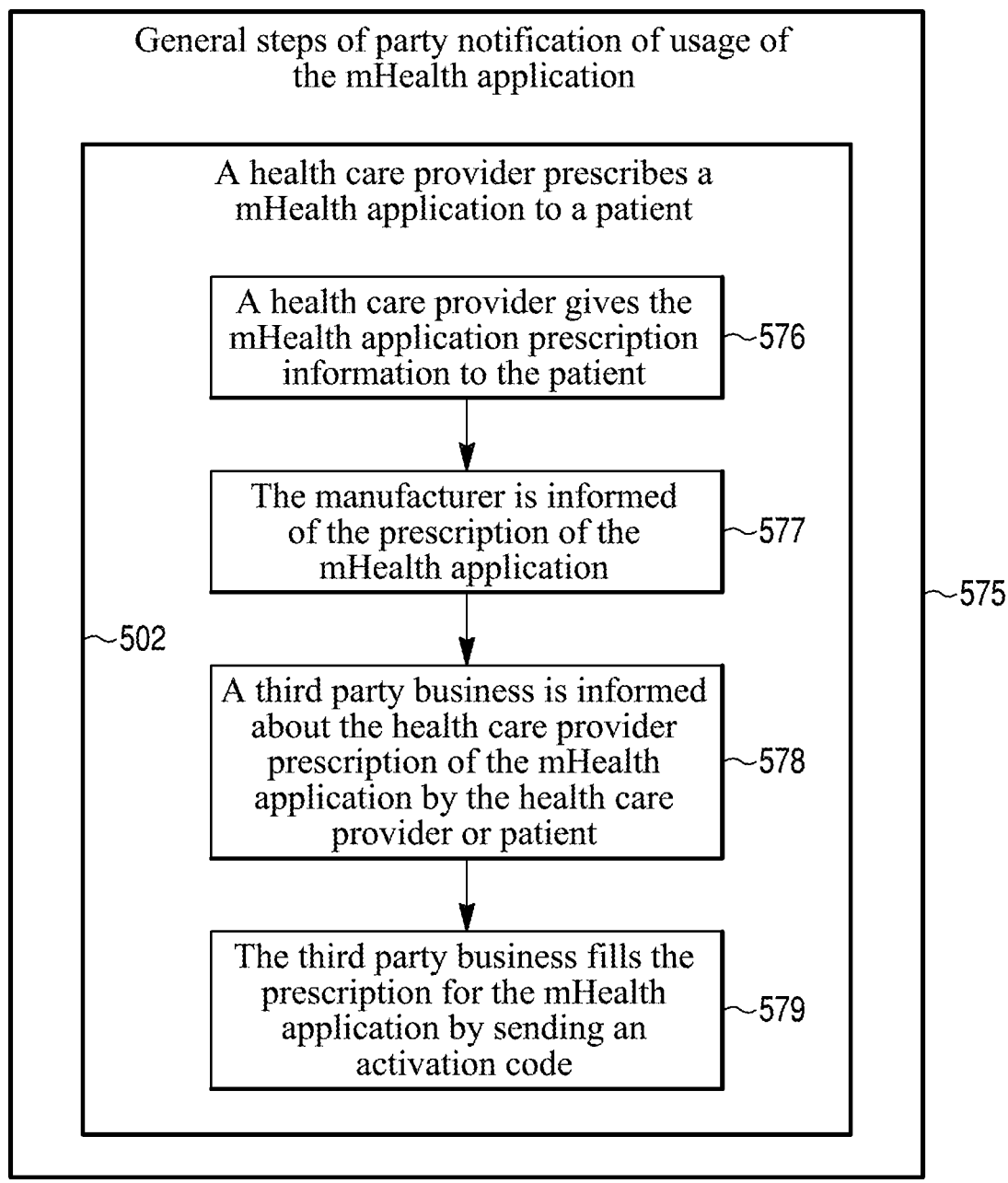
FIG. 5 is a diagrammed method view showing steps of party notification of usage of the mobile health application, according to an exemplary embodiment of the present disclosure.

FIG. 5 shows sub steps of step 502 shown in FIG. 1 as method 575. In step 576, the healthcare provider 7 may electronically send the mHealth application 1 prescription information to the patient 8 via the network 32. The manufacturer 37 may be informed of the prescription of the mHealth application 1 at step 577 via any suitable manner, e.g., email, updating an online database, etc. A third party business 35 may be informed of the prescription of the mHealth application 1 by the healthcare provider 7 or patient 8 at step 578. At step 579, the third party business 35 may fill the prescription for mHealth application 1 by providing the patient 8 an activation code 15 or other suitable means known in the art.

Figure 11:
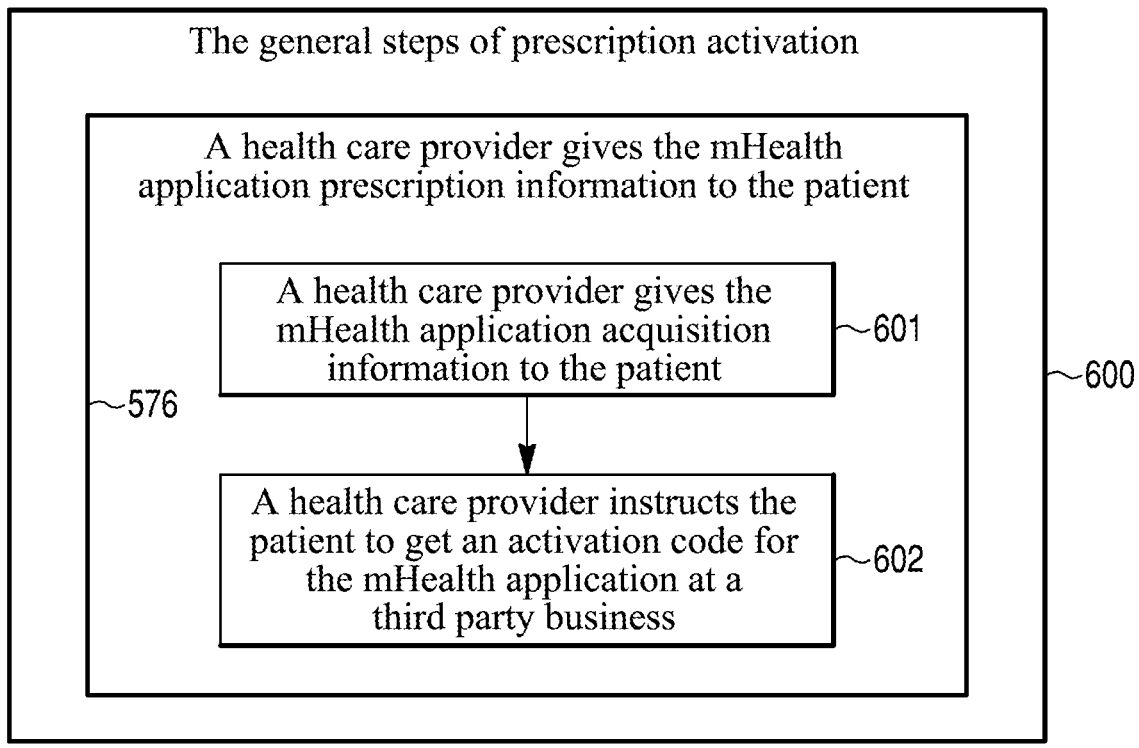
FIG. 11 is a diagrammed method view showing steps of prescription activation, according to an exemplary embodiment of the present disclosure.

Referring now to FIG. 11, step 576 of method 575 may include sub steps collectively referred to as method 600. For example, at step 601 the healthcare provider 7 may send the mHealth application 1 acquisition information to a patient 8. At step 602, the healthcare provider 7 may instruct the patient 8 to retrieve an activation code 15 for the mHealth application 1 at a third party business 35, such as pharmacy, healthcare clinic, laboratory, or any other suitable location.

Figure 12:
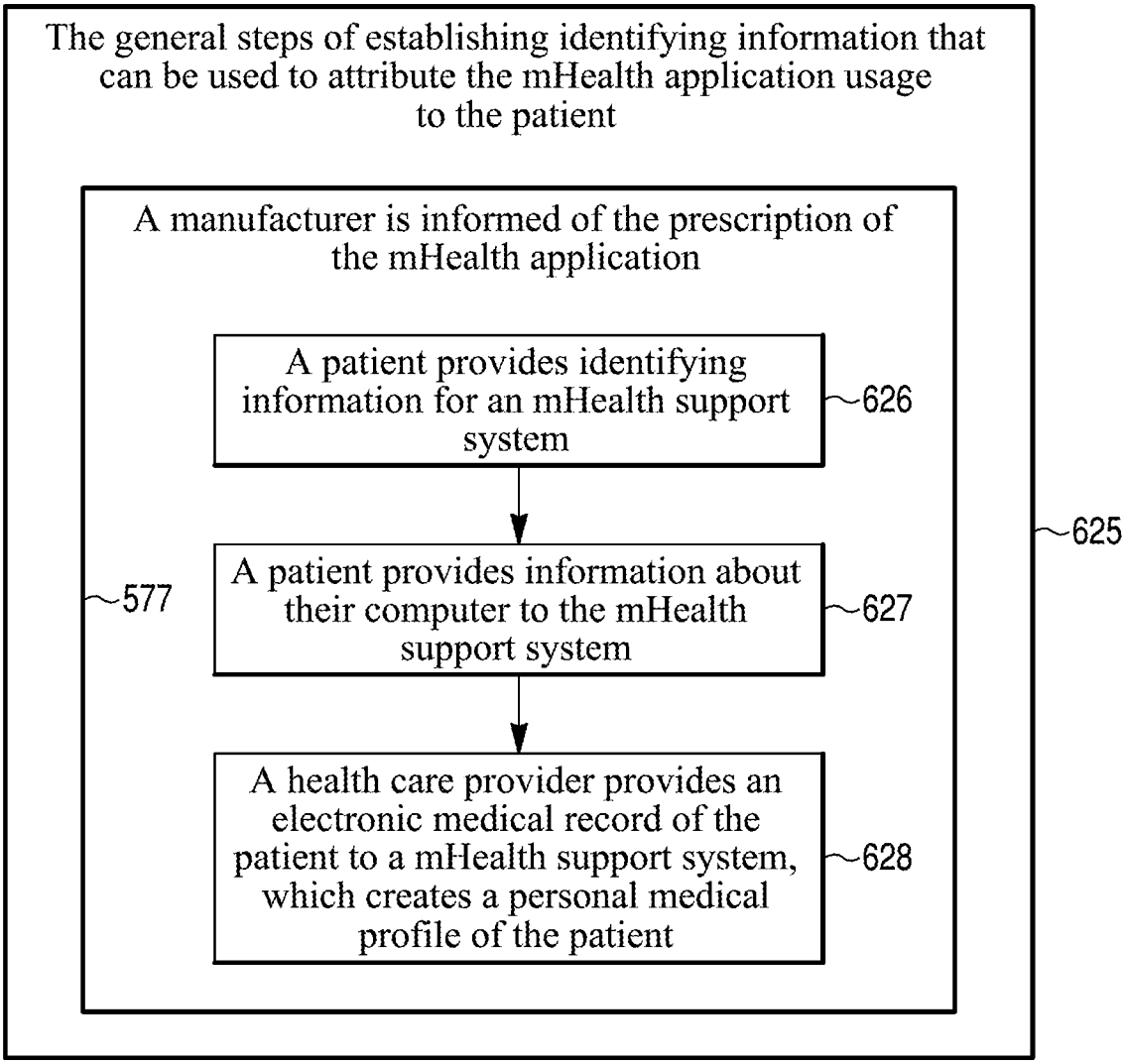
FIG. 12 is a diagrammed method view showing steps of establishing identifying information that can be used to attribute the mobile health application usage to a patient, according to an exemplary embodiment of the present disclosure.

Method 625 as shown in FIG. 12 shows sub steps of step 577. For example, method 625 includes a step 626 in which the patient 8 may provide identifying information 11 for an mHealth support system 23. At step 627, the patient 8 may provide information about their electronic device 19 to the mHealth support system 23. At step 628, the healthcare provider 7 may provide an electronic medical record 14 of the patient 8 to an mHealth support system 23 affiliated with the manufacturer 37, which may create an electronic personal medical profile 21 of patient 8.

Figure 6:
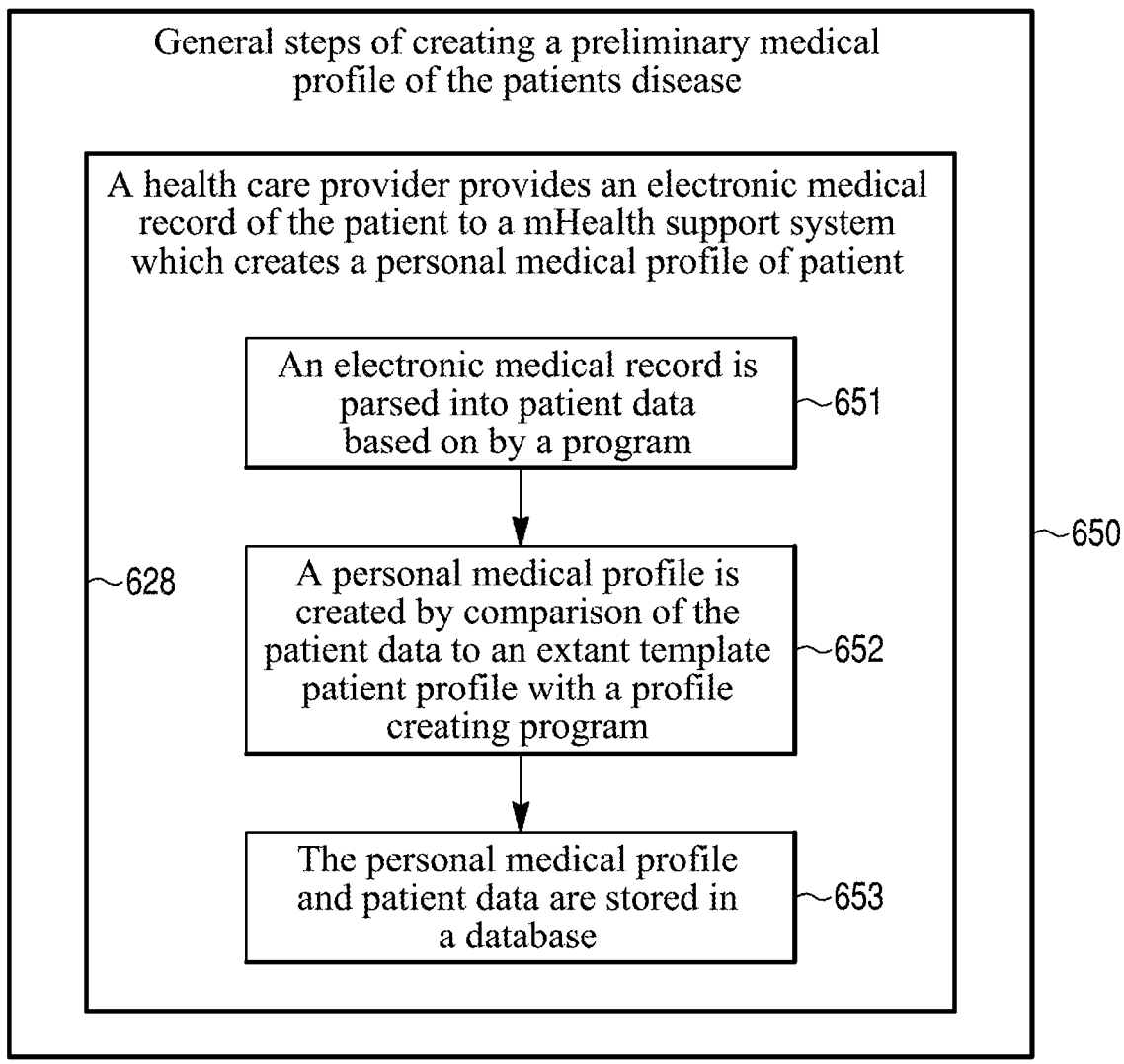
FIG. 6 is a diagrammed method view showing steps of creating a preliminary medical profile of the patient's disease, according to an exemplary embodiment of the present disclosure.

As shown in FIG. 6, step 628 may include sub steps collectively referred to as method 650. For example, step 651 may include parsing the electronic medical record 14 into the patient data based on a program 33. At step 652, the personal medical profile 21 may be created by comparison of the patient data to an existing template patient profile 22 with a profile-creating program 20. At step 653, the personal medical profile 21 and patient data may be stored in a database 30 for reference and modification during mHealth application 1 usage.

Figure 7:
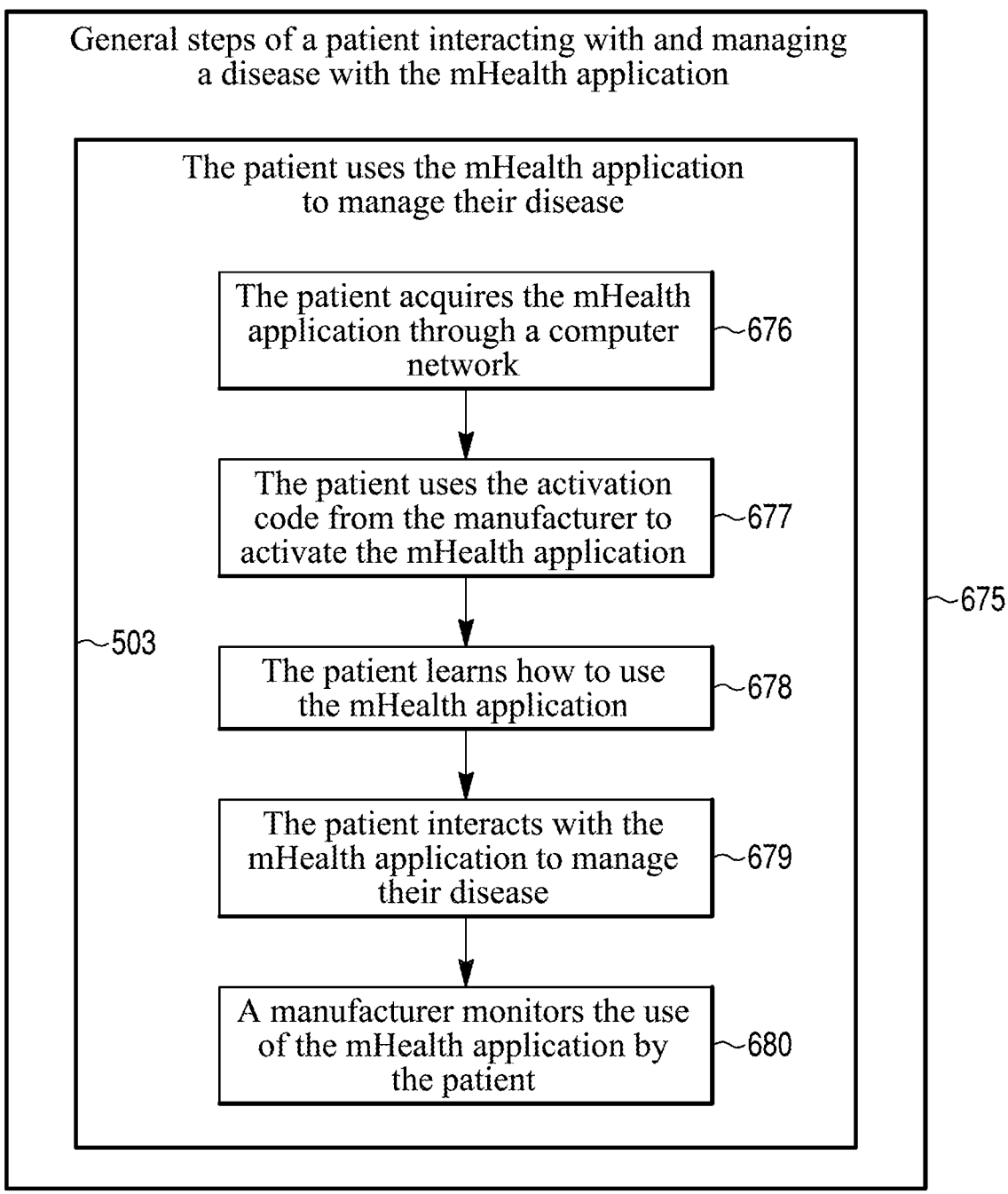
FIG. 7 is a diagrammed method view showing steps of patient interactions with and management of a disease with the mobile health application, according to an exemplary embodiment of the present disclosure.

FIG. 7 shows sub steps of step 503 shown in FIG. 2. The sub steps of step 503 are collectively referred to as method 675. The steps may include the patient 8 acquiring the mHealth application 1 on the patient's electronic device 19 via a computer network 32, such as the Internet at step 676. The patient 8 may use the activation code 15 received from the manufacturer 37 to activate the mHealth application 1 at step 677. At step 678, the patient 8 may learn how to use the mHealth application 1 via instructional information received from the patient's electronic device 19 connected to the network 32. The instructional information may be in any suitable form. For example, a text message (SMS or any other form), video tutorial, slide show, animation, or any other manner. At step 679, the patient 8 may interact with the mHealth application 1 using their electronic device 19 to manage their disease 2. At step 680, the manufacturer 37 may monitor the use of the mHealth application 1 by the patient 8 by sending and receiving data from the patient's electronic device 19.

Figure 8:
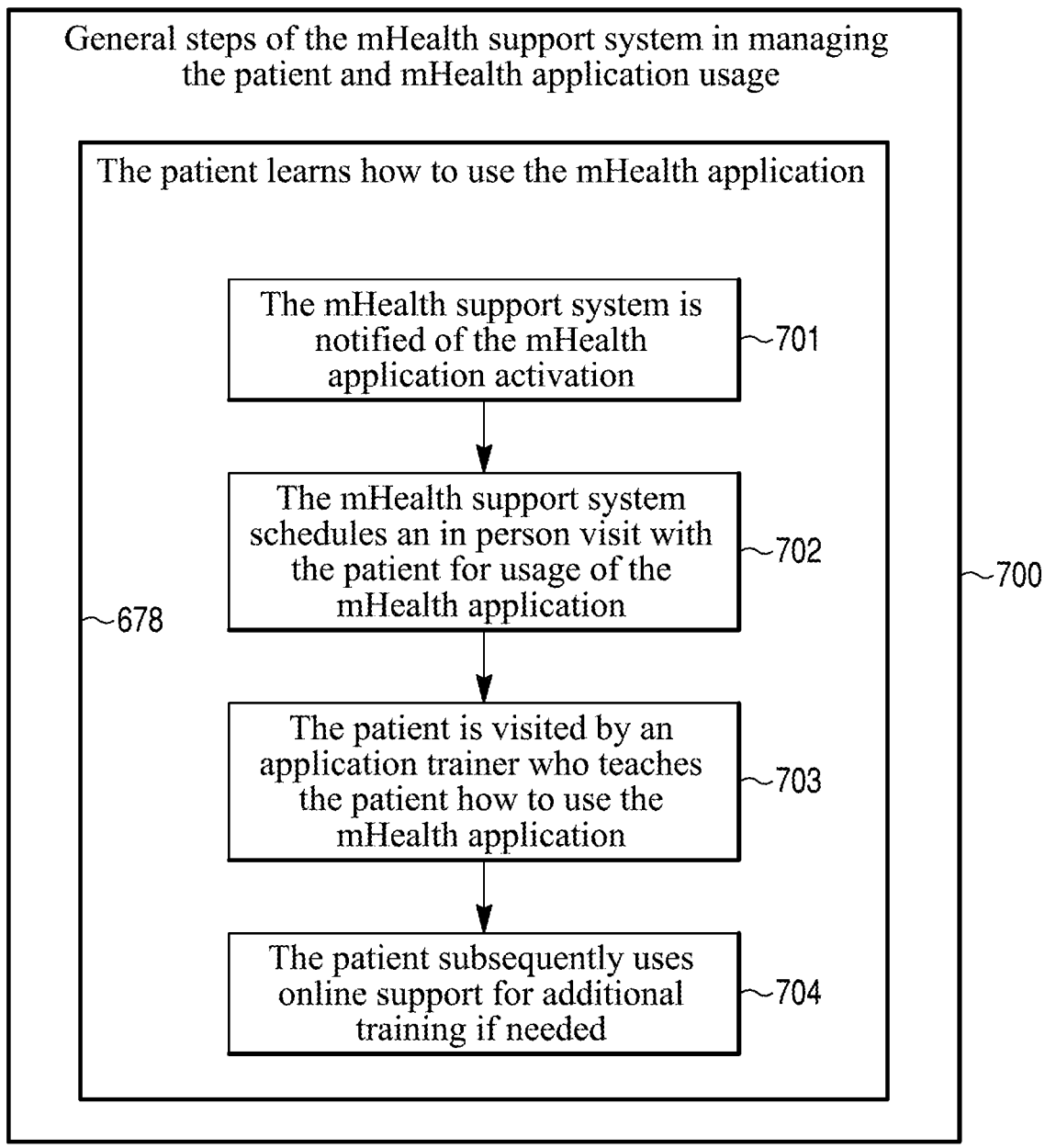
FIG. 8 is a diagrammed method view showing steps of the mobile health support system in managing the patient and mobile health application usage, according to an exemplary embodiment of the present disclosure.

FIG. 8 shows method 700 showing sub steps of step 678. For example, at step 701, the mHealth support system 23 may be notified when the mHealth application 1 is activated. Further, the mHealth support system 23 may schedule an in person visit or any other meeting (e.g., via phone or video conference, etc.,) with the patient 8 for demonstrating, instructing, and/or verifying proper usage of the mHealth application 1, at step 702. The patient 8 may be visited or otherwise contacted by an application trainer 24 who may teach the patient 8 how to use the mHealth application 1, at step 703. The patient 8 subsequently may use online support 25 for additional training if needed, at step 704.

Figure 9:
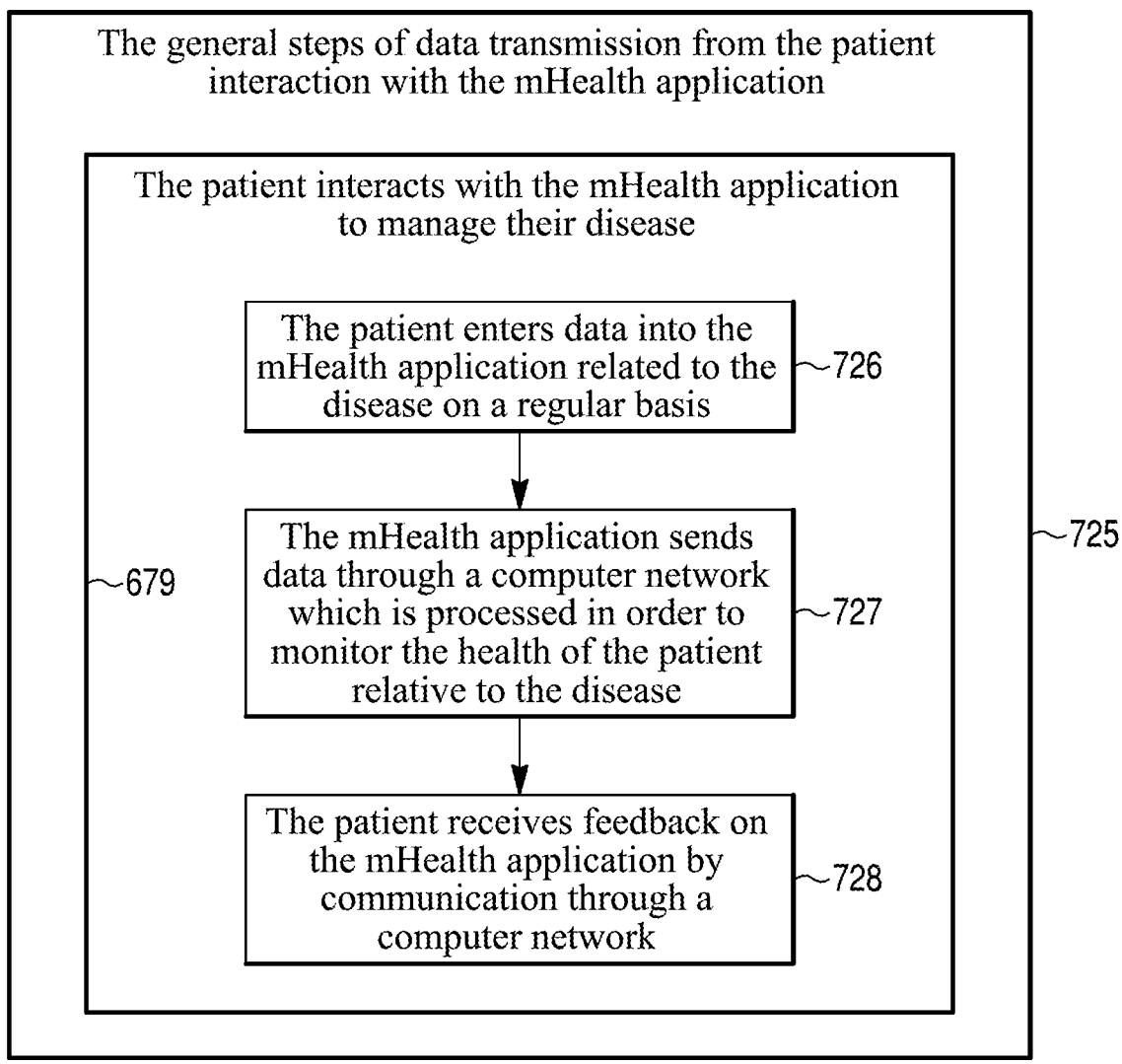
FIG. 9 is a diagrammed method view showing steps of data transmission from the patient interaction with the mobile health application, according to an exemplary embodiment of the present disclosure.

Step 679 shown in FIG. 6 may have several sub steps shown in FIG. 9 as method 725. For example, step 726 may include a patient 8 entering data into the mHealth application 1 related to disease 2 on a regular or otherwise periodic basis. At step 727, the mHealth application 1, which may use a client server model 34, may send data through a computer network 32, which may then be analyzed on the server side 31 and processed in order to monitor the health of the patient 8 relative to the disease 2. At step 728, patient 8 may receive feedback on the mHealth application 1 by communication through the network 32.

Figure 10:
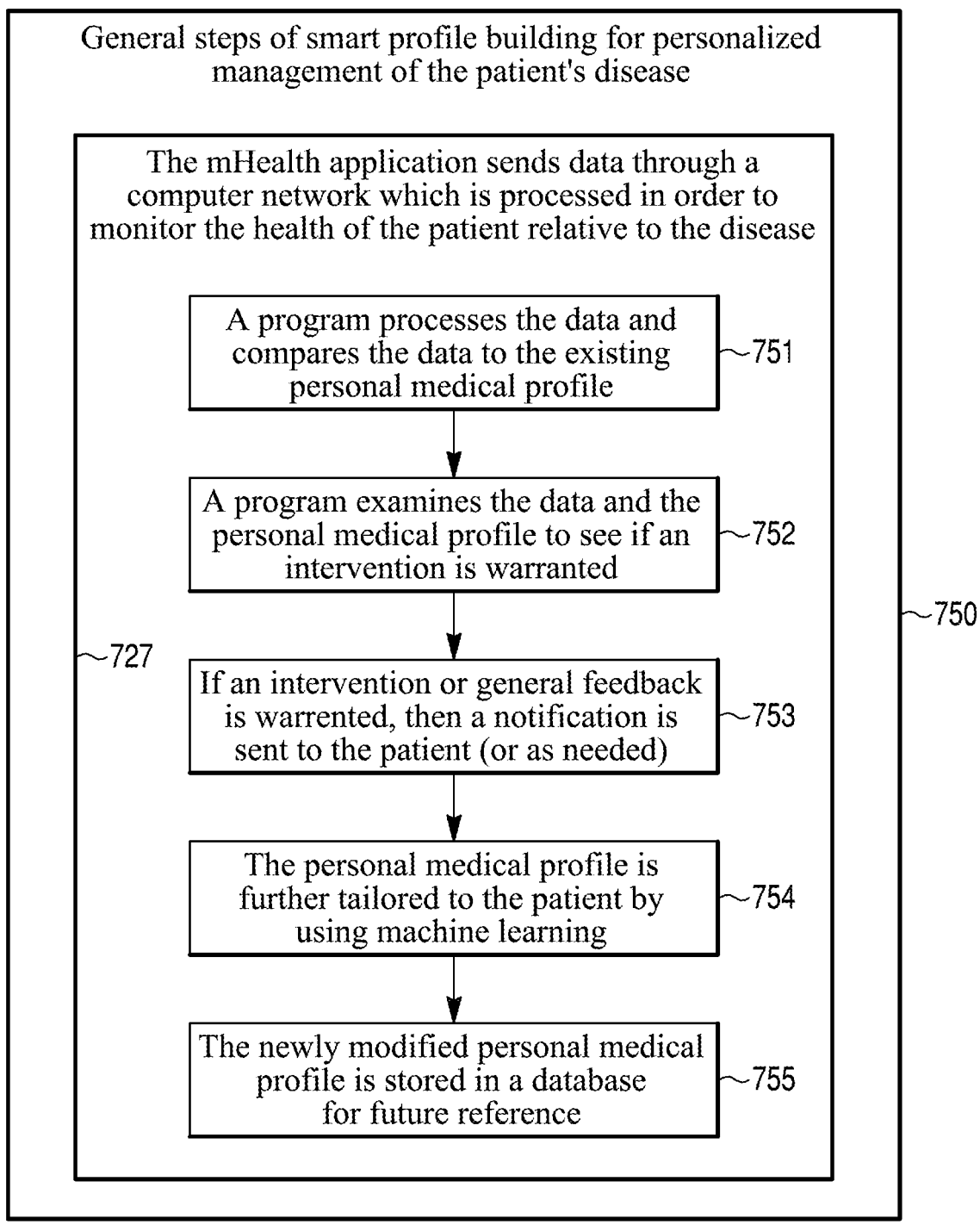
FIG. 10 is a diagrammed method view showing steps of smart profile building for personalized management of the patient's disease, according to an exemplary embodiment of the present disclosure.

FIG. 10 shows sub steps of step 727 as method 750. Method 750 includes sub step 751 of the mHealth application 1 sending data to the server 29, and at step 752 the program 33 processes the data and compares the data to the existing personal medical profile 21. Step 753 includes examining data and the personal medical profile 21 to assess whether an intervention 27 is warranted. At step 754, if an intervention 27 or general feedback is warranted, information may be sent to the patient 8, caregiver or healthcare provider as needed. The personal medical profile 21 may further be tailored to the patient at step 755 by using programs 33 having machine learning algorithms 26. The newly modified personal medical profile 21 may be stored in a database 30 for future access and reference, at step 756.

Figure 13:
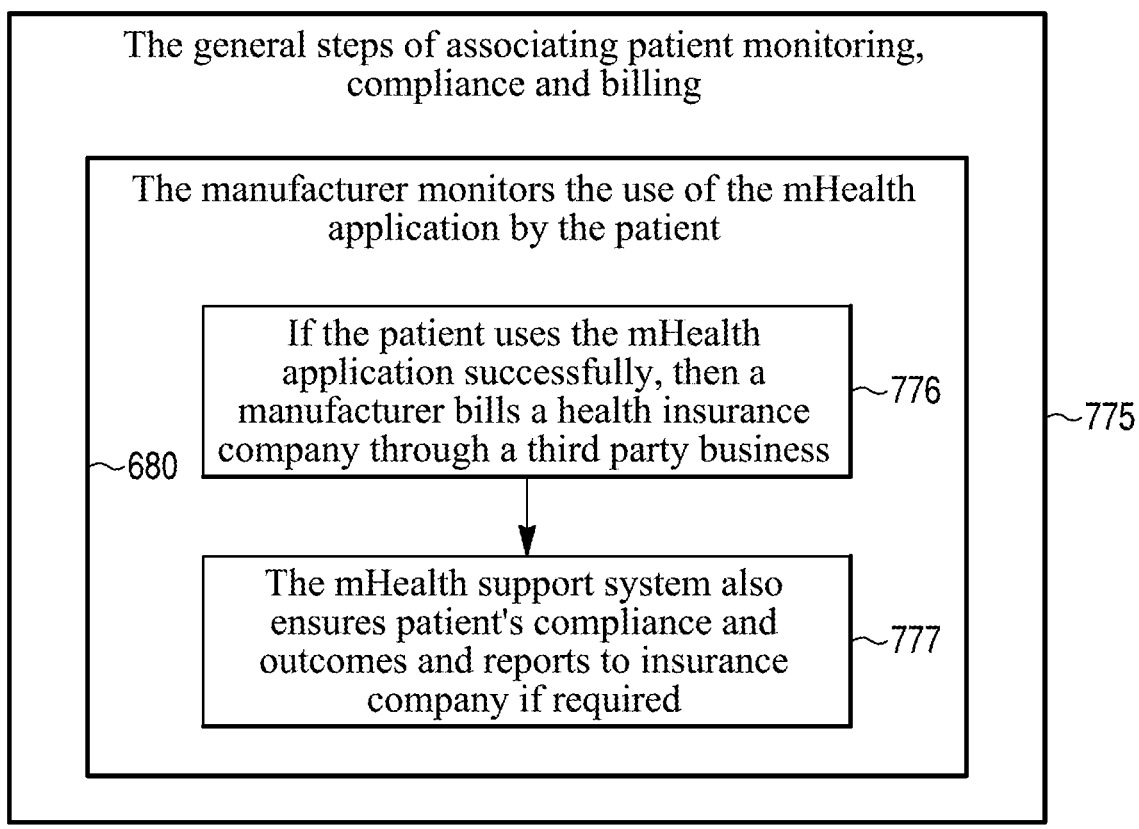
FIG. 13 is a diagrammed method view showing steps of associating patient monitoring, compliance, and billing, according to an exemplary embodiment of the present disclosure.

FIG. 13 shows method 775, which includes sub steps of step 680. The steps included in method 775 may include step 776 of the manufacturer 37 billing the health insurance company 17 through the third party business 35 if the patient 8 uses the mHealth application 1 successfully. Step 777 includes the manufacturer 37 ensuring the patient's compliance and outcomes and reporting compliance to the insurance company 17, if required.

The disclosure comprises numerous terms that may be necessary to define the scope for purposes of interpretation. The definition of these terms allows numerous embodiments that may arise, rather than just the preferred embodiment. The terms are as follows: the mHealth application 1, disease 2, chronic disease 3, software development 12, the computer network 32, software 6, healthcare provider 7, patient 8, pharmacy practice 9, pharmacy 10, identifying information 11, national provider identifier 13, electronic medical record 14, activation code 15, pharmaceutical company 16, health insurance company 17, national drug code 18, electronic device 19, profile creating program 20, personal medical profile 21, template patient profile 22, mHealth support system 23, application trainer 24, online support 25, machine learning 26, intervention 27, programming 28, server 29, database 30, server side 31, computer network 32, program 33, client server model 34, third party business 35, retail store 36, and the manufacturer 37.

The term mHealth application 1 is broadly thought to include, but not limited to, an application on an electronic device 19, for use with medicine and public health. Some embodiments may use an mHealth disease and epidemic outbreak tracing/tracking application 38, an mHealth education application 39, an mHealth diagnostic and treatment support application 40, a mHealth communication and training for healthcare workers application 41, an mHealth remote monitoring application 42, or an mHealth remote data collection application 43 instead of the mHealth application 1. The term disease 2 is thought to encompass, but is not limited to, a medical condition associated with specific symptoms and signs which may also be a chronic disease 3. The term chronic disease 3 is thought to encompass, but is not limited to, a human health condition or disease that is persistent or otherwise long lasting in its effects (when the course of the disease lasts for, e.g., more than three months). In some embodiments the chronic disease may include (but is not limited to) Diabetes, Asthma, Cancer, Mental illness, COPD and/or Hypertension. In most embodiments, it is thought that the healthcare provider 7 may be a doctor 65; however, it is possible that in the future an advanced practice registered nurse 66, physician's assistant 67, or any other suitable healthcare professional could fill this role. The term patient 8 is thought to encompass, but is not limited to, a recipient of health care services. In some embodiments, one can contemplate that the patient 8 also may be an inpatient 68, an outpatient 69, a health care consumer 70, a health consumer 71, or an assisted living resident 72.

The term software development 12 is thought to encompass, but is not limited to, the activity of computer programming, which is the process of writing and maintaining the source code and includes all that is involved between the conception of the desired software through to the final manifestation of the software in a planned and structured process. The term computer network 32 is broadly thought to include, but is not limited to, a telecommunications network that allows computers to exchange data. In some versions, functionally, the computer network 32 could be either a personal area network 120, a wireless personal area network 121, a near-me area network 122, a local area network 123, a wireless local area network 124, a wireless mesh network 125, a wireless metropolitan area network 126, a wireless wide area network 127, a cellular network 128, a home area network 129, a storage area network 130, a campus area network 131, a backbone area network 132, a metropolitan area network 133, a wide area network 134, an enterprise private network 135, a virtual private network 136, an intranet 137, a cloud network, a social network, an extranet 138, a Internetwork 139, or an Internet 140. The term software 6 is thought to encompass a collection of computer programs and related data.

In other embodiments, not just the preferred, the term third party business 35 may include, but is not limited to, a company or business concern other than the manufacturer 37, patient 8, healthcare provider 7 or health insurance company 17 that bills for services and refills the mHealth application 1. In some embodiments, this may be a pharmacy 10 or a retail store 36. One or more pharmacies, retail stores, insurance companies, and/or physicians may access interconnected servers for sending and retrieving data related to one or more patient. The mHealth application 1 may process the requests and exchange of patient information/data, and may regulate the dispensing of pharmaceuticals, medical therapies, medical devices, or other suitable healthcare related products based on access to patient data.

The drug or other prescribed medical product may only be refilled if (e.g. the pharmacy (e.g., third party business, etc.,) receives notification regarding authorization to refill) per the application, it is determined that the patient has used all or a pre-determined amount of the originally prescribed amount of medical product or therapy. In this manner waste, fraud, and/or off-label use of medical products or therapy may be deterred or avoided. Further, the disclosed methods may determine a minimum effective dose or amount of a medical product/therapy, thereby further reducing waste and healthcare related costs as well as avoiding potential side effects, increased de-sensitivity and other potential harms involved with overuse of drugs.

Moreover, the disclosed methods may improve patient compliance with healthcare professional recommendations and treatment plans by providing patients with frequent and real-time information regarding the patient's treatment and effectiveness of the treatment plan. In addition, the interconnectivity of healthcare provider, pharmacy, user application, and other entities may provide improved and quicker access, feedback, and treatment for patients while reducing waste and healthcare costs.

The term manufacturer 37 is thought to encompass, but is not limited to, a person or business concern that creates the mHealth application 1. In some embodiments, manufacturer 37 may include a pharmaceutical company 16. The term retail store 36 is thought to encompass a store that practices the sale of goods and services from individuals or business to a consumer. For examples, a retail store 36 may purchase goods or products in large quantities from manufacturers directly or through a wholesaler, and then sell or resell smaller quantities to the consumer for a profit. The term pharmacy practice 9 is broadly thought to include a practice linking the safe and effective use of pharmaceutical drugs to the practice of the health sciences. The term pharmacy 10 is thought to encompass, but is not limited to, an establishment where pharmacy practice 9 is performed. Alternatively, in other embodiments, the pharmacy 10 may be a community pharmacy 73, a retail pharmacy 74, a hospital or internal pharmacy 75, a clinical pharmacy 76, an ambulatory care pharmacy 77, a compounding pharmacy 78, a consultant pharmacy 79, an internet pharmacy 80, a nuclear pharmacy 81, or a military pharmacy 82. The term pharmaceutical company 16 is thought to encompass a company who develops produces, and markets, devices, therapies, drugs, and/or pharmaceuticals for use in managing disease 2. The term health insurance company 17 is broadly thought to include a company in the business of issuing insurance against the risk of incurring medical expenses among individuals.

The term identifying information 11 is broadly thought to include, but is not limited to, information that can be used on its own or with other information to identify, contact, or locate a single person, or to identify an individual in context. In some versions, the identifying information 11 could be a name, finger print, retina scan, DNA signature, voice profile, biometric profile, email address or user ID, date of birth, home telephone number, cellular telephone number, home address, work address, age, gender, country, or state or other location. An alert may be provided to the healthcare provider, manufacturer, or any other relevant entity, via the network 32, if an unauthorized user is attempting to use the medical product or access the application in an unauthorized manner. The alert may have any suitable form, such as an SMS message, phone voice message, email message, etc.

The term national provider identifier 13 is broadly thought to include, but is not limited to, a National Provider Identifier or NPI, which is a unique 10-digit identification number issued to healthcare providers in the United States by the Centers for Medicare and Medicaid Services (CMS). The term electronic medical record 14 is broadly thought to include electronic health information and may be a representation of all a patients' health related information data that would be typically found in the traditional paper-based records. The term national drug code 18 may include a unique 10-digit, 3-segment numeric identifier assigned to each medication listed under Section 510 of the US Federal Food, Drug, and Cosmetic Act.

The term computer memory 95 is broadly thought to include the physical devices used to store programs (sequences of instructions) or data (e.g., program state information) on a temporary or permanent basis for use in a computer or other digital electronic device. In some embodiments, it is thought that the electronic device 19 also may be a desktop computer, a car information service, a game console, a laptop, a notebook, a palmtop, a tablet, a smartphone, or a smart book. The electronic device 19 may include four or more components respectively defined as the computer central processing unit (CPU), the computer memory, the computer operating system 96, and the computer graphical user interface. The term computer operating system 96 is thought to encompass, but is not limited to, a collection of software that manages computer hardware resources and provides common services for computer programs. The term computer graphical user interface may include a type of user interface that allows users to interact with electronic devices through graphical icons and visual indicators such as secondary notation, as opposed to text-based interfaces, typed command labels or text navigation. The term profile-creating program 20 is thought to encompass a program 33 that creates intervention 27 related parameters based on incoming data from a patient 8. The term personal medical profile 21 is broadly thought to include, but is not limited to, a model generated from a machine learning algorithm 26 based on patient data that has been collected over time. The term template patient profile 22 may include a model generated from a machine learning algorithm 26 based on primary patient data and general knowledge of how the data parameters indicate health or illness as reported by the patient over time.

In one or more other embodiments, the term mHealth support system 23 may include, but is not limited to, a system with a range of patient services to assist patients in the correct use of a mHealth application 1. It includes assistance in planning, installation, training, troubleshooting, maintenance, compatibility, and upgrading of the mHealth application 1. The mHealth support system 23 may or may not be affiliated with the manufacturer 37. The term application trainer 24 is thought to encompass a person knowledgeable of the disease 2 and the mHealth application 1 who assists the patient 8 in learning its uses. The term online support 25 is thought to encompass support structures that provide on-line libraries and tools for self-help and easy troubleshooting solutions to automatically and precisely diagnose and resolve problems and incidents. Alternatively, the online support 25 may be self-support automation or also assisted support automation in some embodiments. The term intervention 27 is broadly thought to include an attempt by the mHealth application 1 to notify one or more entities e.g., the patient 8, healthcare provider 7, or caregiver of a presumptive problem with the management of the disease 2.

In other embodiments, not just the preferred, the term programming 28 may include the comprehensive process that leads from an original formulation of a computing problem to executable programs. The term server 29 is thought to encompass a system (software and suitable computer hardware) that responds to requests across a computer network. The term database 30 is thought to encompass an organized collection of data with a software system designed to allow the definition, creation, querying, update, and administration of databases. The term server side 31 may include operations that are performed by the server in a client-server relationship in computer networking.

In other embodiments, not just the preferred, the term program 33 may include a sequence of instructions, written to perform a specified task with a computer that is executed by the computer central processing unit 94. The term client server model 34 may include structure in computing that partitions tasks or workloads between the providers of a resource or service, called servers, and service requesters, called clients. The term machine-learning algorithm 26 is broadly thought to include a series of systems or programs that can learn from data without having to be explicitly programmed e.g. a neural network.

Alternatively, in other embodiments, the machine learning may be a decision tree learning 109, an association rule learning 110, an artificial neural networks 111, an inductive logic programming 112, a support vector machines 113, a clustering 114, a Bayesian networks 115, a reinforcement learning 116, a representation learning 117, a similarity and metric learning 118, or a sparse Dictionary Learning 119.

Figure 14:
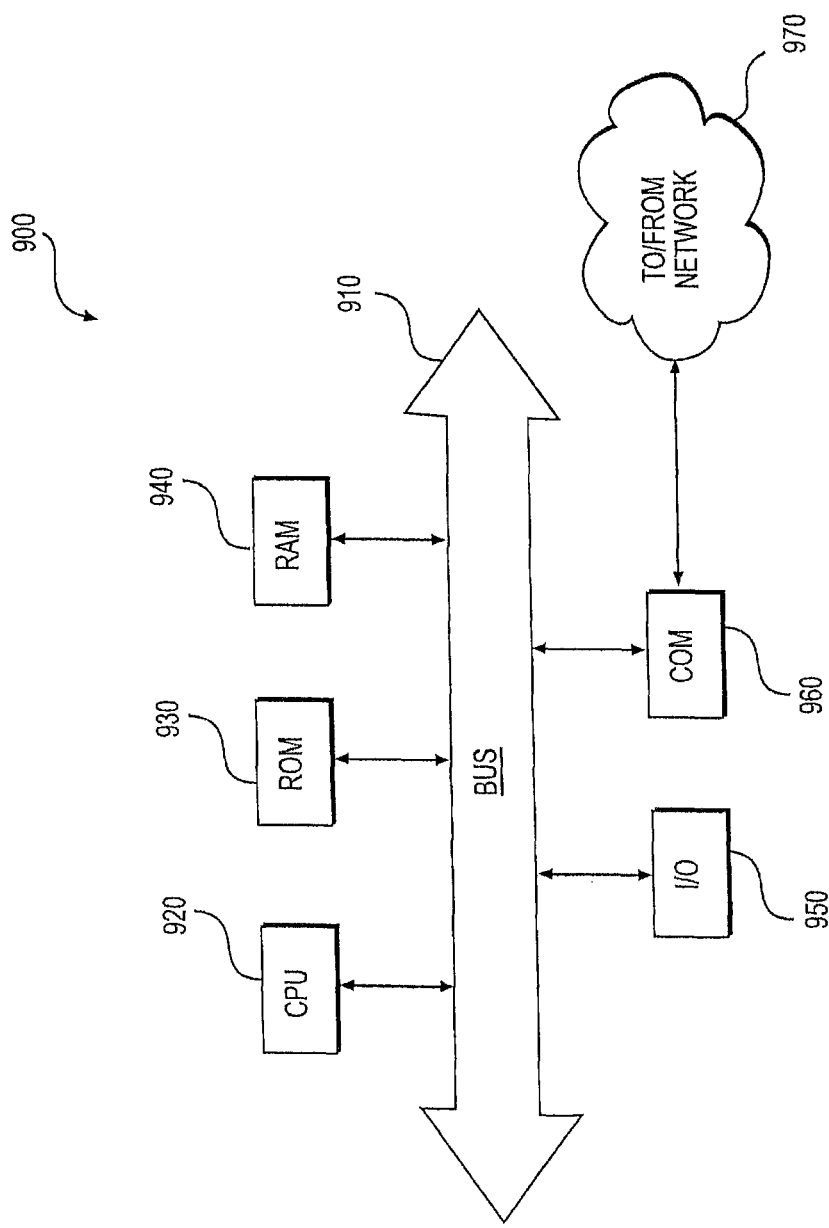
FIG. 14 is a functional block diagram of a computer that may be configured as a host server, for example, to function as a break point server.

FIG. 14 provides a functional block diagram illustration of general-purpose computer hardware platforms. FIG. 14 illustrates a network or host computer platform 900, as typically may be used to implement a server, such as the server 29. It is believed that those skilled in the art are familiar with the structure, programming, and general operation of such computer equipment and as a result, the drawings should be self-explanatory.

A platform for a server or the like 900, for example, may include a data communication interface for packet data communication 960. The platform also may include a central processing unit (CPU) 920, in the form of one or more processors, for executing program instructions. The platform typically includes an internal communication bus 910, program storage, and data storage for various data files to be processed and/or communicated by the platform such as ROM 930 and RAM 940, although the server 900 often receives programming and data via network communications 970. The hardware elements, operating systems, and programming languages of such equipment are conventional in nature, and it is presumed that those skilled in the art are adequately familiar therewith. The server 900 also may include input and output ports 950 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for providing and monitoring user compliance with a regimen over a network, the method comprising:
   analyzing properties of a disease based on patient data, wherein the properties of the disease comprise temporary, chronic, and persistent symptoms associated with the disease, a duration associated with the disease, and treatments associated with the disease;
   providing a prescription to a third party that generates an activation code based on the prescription via a third party server unaffiliated with a health care provider;
   providing an instruction to a user to obtain the activation code, for an application, from the third party, wherein the user is one of an inpatient, an outpatient, a health care consumer, or an assisted living resident;
   generating a user personal medical profile based on receiving patient identification information, user device information, and an electronic medical record of the patient, wherein the user personal medical profile is further based on parsing the electronic medical record into user data and comparing the user data to one or more existing template patient profiles, and wherein the user personal medical profile is generated based on a model generated from a machine learning algorithm, wherein the machine learning algorithm includes one or more of a decision tree learning algorithm, an association rule learning algorithm, an artificial neural network, an inductive logic programming algorithm, a support vector machines based algorithm, a clustering algorithm, a Bayesian networks algorithm, a reinforcement learning algorithm, a representation learning algorithm, a similarity and metric learning algorithm, or a sparse dictionary learning algorithm;
   storing the user personal medical profile and the user data, wherein the stored personal medical profile and the user data are accessed by the application for use and wherein the stored personal medical profile and the user data are updated by the application;
   applying the activation code received from the third party;
   permitting user access to the application only after the applied activation code being confirmed via the application;
   generating the application for operation on a user device having a graphical user interface (GUI), the application including an input for the user to input data via the GUI for use in evaluating compliance with the regimen, wherein the user device is one of a desktop computer, a game console, a laptop, a notebook, a palmtop, a tablet, a smartphone, or a smart book;
   providing instructional information via the user device, the instructional information including instructions for use of the application and being provided via one or more of a text message, a video tutorial, a slide show, and an animation;
   receiving patient entries input via the GUI, over the network;
   analyzing patient entries for compliance with the regimen based on the patient entries, wherein analyzing the patient entries comprises comparing the patient entries to the user personal medical profile to determine that one or more of a change or an action is needed;

providing feedback, via the application, to the patient, based on analyzing the patient entries;

processing a request for one or more healthcare products via the application, wherein the one or more healthcare products may be selected from a pharmaceutical, a medical therapy, or a medical device;

activating the application based on receiving, over the network, an instruction to activate the application from the compliance entity;

automatically updating the application based on the patient entries;

determining unauthorized use of the application based on one or more of an unauthorized user, an unauthorized device, or an unauthorized use;

generating an alert, via the network, based on determining the unauthorized use of the application and providing the alert to the provider;

sending, via the network, a report to the provider, based on analyzing the patient entries;

receiving, over the network, instructions for the regimen;

receiving user compliance data from the application over the network based on the patient entries; and generating electronic feedback to the user based on electronic processing of the user compliance data.

2. The computer-implemented method of claim 1, further comprising acquiring a national drug code number form a regulatory entity.

3. The computer-implemented method of claim 2, further comprising generating a software based on analyzing the properties of the disease.

4. The computer-implemented method of claim 3, acquiring a national provider identifier (NPI), wherein an application based on the software is prescribed, via a prescription from the health care provider, based on at least one of the national drug code number and the NPI.

5. The computer-implemented method of claim 1, further comprising providing a report to a compliance entity based on analyzing the patient entries, wherein the report comprises an analysis of patient compliance with the regimen, wherein the compliance entity is an insurance company.

6. A system for providing and monitoring compliance with a regimen over a network, the system comprising:

a data storage device storing instructions for causing computer servers and user devices to generate, provide, or evaluate compliance with, the regimen; and a processing device configured to execute instructions to perform a method of:

analyzing properties of a disease based on patient data, wherein the properties of the disease comprise temporary, chronic, and persistent symptoms associated with the disease, a duration associated with the disease, and treatments associated with the disease;

providing a prescription to a third party, that generates an activation code based on the prescription via a third party server unaffiliated with a health care provider;

providing an instruction to a user to obtain the activation code, for an application, from the third party;

generating a user personal medical profile based on receiving patient identification information, user device information, and an electronic medical record of the patient, wherein the user personal medical profile is further based on parsing the electronic medical record into user data and comparing the user data to one or more existing template patient profiles, and wherein the user personal medical profile is generated based on a model generated from a machine learning algorithm;

storing the user personal medical profile and the user data, wherein the stored personal medical profile and the user data are accessed by the application for use and wherein the stored personal medical profile and the user data are updated by the application;

applying the activation code received from the third party;

permitting user access to the application only after the applied activation code being confirmed via the application;

generating the application for operation on a user device having a graphical user interface (GUI), the application including an input for the user to input data via the GUI for use in evaluating compliance with the regimen;

providing instructional information via the user device, the instructional information including instructions for use of the application and being provided via one or more of a text message, a video tutorial, a slide show, and an animation;

receiving patient entries input via the GUI, over the network;

analyzing patient entries for compliance with the regimen based on the patient entries, wherein analyzing the patient entries comprises comparing the patient entries to the user personal medical profile to determine that one or more of a change or an action is needed;

providing feedback, via the application, to the patient, based on analyzing the patient entries;

processing a request for one or more healthcare products via the application, wherein the one or more healthcare products may be selected from a pharmaceutical, a medical therapy, or a medical device;

providing a report to a compliance entity based on analyzing the patient entries, wherein the report comprises an analysis of patient compliance with the regimen; and receiving user compliance data from the application over the network based on the patient entries.

7. The system of claim 6, wherein the processor is further configured to execute instructions to provide, via the network, a notification to a dispenser to refill a prescription for the application based on analyzing the patient entries.

8. The system of claim 6, wherein the compliance entity is an insurance company and further comprising activating the application based on receiving, over the network, instructions from the compliance entity.

9. The system of claim 6, wherein the processing device is further configured to execute instructions to send, via the network, a report to the user, based on analyzing the patient entries.

10. The system of claim 6, wherein the processing device is further configured to execute instructions to automatically update the application based on the patient entries.

11. The system of claim 6, wherein the processing device is further configured to receive, over the network, instructions for the regimen.

12. The system of claim 6, further comprising generating a software based on analyzing the properties of the disease.

13. The system of claim 12, further comprising acquiring a national drug code number form a regulatory entity.

14. The system of claim 13, further comprising acquiring a national provider identifier (NPI), wherein an application based on the software is prescribed, via a prescription form the health care provider based on at least one of the national drug code number and the NPI.

15. A non-transitory computer-readable medium storing instructions that, when executed by a processor, cause the processor to provide and monitor compliance with a regimen over a network, the instructions comprising:

analyzing properties of a disease based on patient data, wherein the properties of the disease comprise temporary, chronic, and persistent symptoms associated with the disease, a duration associated with the disease, and treatments associated with the disease;

providing a prescription to a third party, that generates an activation code based on the prescription via a third party server unaffiliated with a health care provider;

providing an instruction to a user to obtain the activation code, for an application, from the third party;

generating a user personal medical profile based on receiving patient identification information, user device information, and an electronic medical record of the patient, wherein the user personal medical profile is further based on parsing the electronic medical record into user data and comparing the user data to one or more existing template patient profiles, and wherein the user personal medical profile is generated based on a model generated from a machine learning algorithm;

storing the user personal medical profile and the user data, wherein the stored personal medical profile and the user data are accessed by the application for use and wherein the stored personal medical profile and the user data are updated by the application;

applying the activation code received from the third party;

permitting user access to the application only after the applied activation code being confirmed via the application;

generating the application for operation on a user device having a graphical user interface (GUI), the application including an input for the user to input data via the GUI for use in evaluating compliance with the regimen;

providing instructional information via the user device, the instructional information including instructions for use of the application and being provided via one or more of a text message, a video tutorial, a slide show, and an animation;

receiving patient entries input via the GUI, over the network;

analyzing patient entries for compliance with the regimen based on the patient entries, wherein analyzing the patient entries comprises comparing the patient entries to the user personal medical profile to determine that one or more of a change or an action is needed;

providing feedback, via the application, to the patient, based on analyzing the patient entries;

processing a request for one or more healthcare products via the application, wherein the one or more healthcare products may be selected from a pharmaceutical, a medical therapy, or a medical device;

providing a report to a compliance entity based on analyzing the patient entries, wherein the report comprises an analysis of patient compliance with the regimen; and receiving user compliance data from the application over the network based on the patient entries.

16. The non-transitory computer-readable medium of claim 15, further comprising generating a software based on analyzing the properties of the disease.

17. The non-transitory computer-readable medium of claim 16, further comprising acquiring a national drug code number form a regulatory entity.

18. The non-transitory computer-readable medium of claim 17, further comprising acquiring a national provider identifier (NPI), wherein the application based on the software is prescribed, via the prescription from the health care provider, based on at least one of the national drug code number and the NPI.

19. The non-transitory computer-readable medium of claim 15, wherein the processor is further configured to execute instructions to automatically update the application based on the patient entries.

20. The non-transitory computer-readable medium of claim 15, wherein the processor is further configured to receive, over the network, instructions for the regimen.

* * * * *